United States Patent
Von Der Saal et al.

Patent Number: 5,414,088
Date of Patent: May 9, 1995

[54] 2-BICYCLOBENZIMIDAZOLES, PROCESSES FOR THEIR PREPARATION AND MEDICAMENTS CONTAINING THESE COMPOUNDS

[75] Inventors: Wolfgang Von Der Saal, Weinheim; Harald Zilch, Mannheim; Erwin Böhm, Ladenburg, all of Germany

[73] Assignee: Boehringer Mannheim GmbH, Mannheim, Germany

[21] Appl. No.: 847,060

[22] PCT Filed: Sep. 4, 1990

[86] PCT No.: PCT/EP90/01663
§ 371 Date: Apr. 14, 1992
§ 102(e) Date: Apr. 14, 1992

[87] PCT Pub. No.: WO91/04974
PCT Pub. Date: Apr. 18, 1991

[51] Int. Cl.⁶ .............. C07D 215/227; C07D 235/18; A61K 31/415; A61K 31/47
[52] U.S. Cl. ........................... 546/158; 546/157; 546/18
[58] Field of Search .............. 514/312; 546/158, 157, 546/18

[56] References Cited
U.S. PATENT DOCUMENTS
4,898,872 2/1990 Campbell et al. .............. 514/303

FOREIGN PATENT DOCUMENTS
81299 5/1988 Australia .
268178 5/1988 European Pat. Off. .
290153 11/1988 European Pat. Off. .

OTHER PUBLICATIONS
Chemical Abstracts 110(17) 154319n, 1989.

*Primary Examiner*—C. Warren Ivy
*Assistant Examiner*—D. Margaret M. Mach
*Attorney, Agent, or Firm*—Felfe & Lynch

[57] ABSTRACT

The invention concerns compounds of formula I

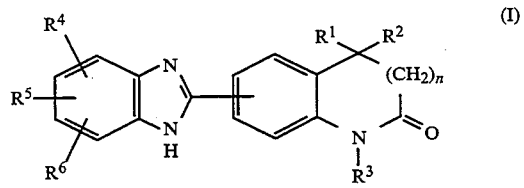

where $R^1$ is hydrogen, $C_1$–$C_6$-alkyl, $C_2$–$C_6$-alkenyl or $C_3$–$C_7$-cycloalkyl, $R^2$ is $C_1$–$C_6$-alkyl, $C_2$–$C_6$-alkenyl, cyano, carboxy [carbonyl substituted by hydroxyl], $C_1$–$C_6$-alkyl, $C_1$–$C_6$-alkoxy, amino, $C_1$–$C_6$-alkylamino, di-$C_1$–$C_6$-alkylamino or hydrazino or $R^1$ and $R^2$ together are $C_2$–$C_6$-alkylidene or $C_3$–$C_6$-cycloalkylidene or $R^1$ and $R^2$, together with the carbon atoms to which they are attached, form a $C_3$–$C_7$-spirocycle, n is 0 or 1, $R^3$ is hydrogen, $C_1$–$C_8$-alkyl, $C_2$–$C_6$-alkenyl, $C_2$–$C_6$-alkynyl, $C_3$–$C_7$-cycloalkyl, benzyl, carboxy-$C_1$–$C_6$-alkyl, $C_1$–$C_6$-alkyloxycarbonyl-$C_1$–$C_6$-alkyl or di-$C_1$–$C_6$-alkyloxophosphinyl-$C_1$–$C_6$-alkyl and $R^4$–$R^6$ are as in the specification. These compounds of formula I serve for the preparation of medicaments to inhibit erythrocyte and thrombocyte aggregation. Therefore, these compounds are useful for the treatment of diseases where these aggregations occur such as arterial occlusive or ischaemic conditions, venous insufficiency or diabetes mellitus.

13 Claims, No Drawings

2-BICYCLOBENZIMIDAZOLES, PROCESSES FOR THEIR PREPARATION AND MEDICAMENTS CONTAINING THESE COMPOUNDS

The present invention concerns compounds of the general formula I

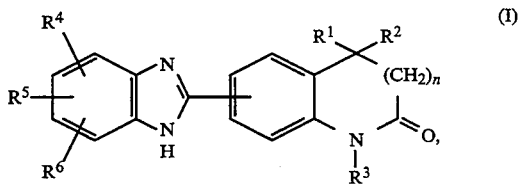

in which $R^1$ signifies a hydrogen atom, a $C_1$–$C_6$-alkyl, $C_2$–$C_6$-alkenyl or a $C_3$–$C_7$-cycloalkyl group, $R^2$ signifies a $C_1$–$C_6$-alkyl, $C_2$–$C_6$-alkenyl or cyano group, a carbonyl group substituted by a hydroxyl, $C_1$–$C_6$-alkyl, $C_1$–$C_6$-alkoxy, amino, $C_1$–$C_6$-alkylamino, di-$C_1$–$C_6$-alkylamino or hydrazino group or $R^1$ and $R^2$ together represent a $C_2$–$C_6$-alkylidene or $C_3$–$C_6$-cycloalkylidene group or $R^1$ and $R^2$, together with the carbon atom to which they are attached, form a $C_3$–$C_7$-spirocycle, n can be equal to 0 or 1, $R^3$ signifies a hydrogen atom, a $C_1$–$C_8$-alkyl, $C_2$–$C_6$-alkenyl, $C_2$–$C_6$-alkynyl, $C_3$–$C_7$-cycloalkyl, benzyl, carboxy-$C_1$–$C_6$-alkyl, $C_1$–$C_6$-alkyloxycarbonyl-$C_1$–$C_6$-alkyl or di-$C_1$–$C_6$-alkyloxophosphinyl-$C_1$–$C_6$-alkyl group, $R^4$, $R^5$, $R^6$ can be the same or different and each can be hydrogen, a $C_1$–$C_7$-alkanesulphonyloxy, trifluoromethanesulphonyloxy, $C_1$–$C_7$-alkanesulphonylamino, trifluoromethanesulphonylamino, N-$C_1$–$C_7$-alkyl-$C_1$–$C_7$-alkanesulphonylamino, phenylsulphonylamino, $C_1$–$C_7$-alkylsulphenylmethyl, $C_1$–$C_7$-alkylsulphinylmethyl or $C_1$–$C_7$-alkylsulphonylmethyl group, a carbonyl group substituted by a hydroxyl, $C_1$–$C_7$-alkoxy, $C_1$–$C_7$-alkyl, amino, $C_1$–$C_7$-alkylamino or di-$C_1$–$C_7$-alkylamino group, a sulphonyl group substituted by an amino, $C_1$–$C_7$-alkylamino, di-$C_1$–$C_7$-alkylamino, morphoino, thiomorpholino, pyrrolidino, piperidino or hexamethyleneimino group, a $C_1$–$C_7$-alkylcarbonylamino, $C_1$–$C_7$-alkylcarbonyloxy, aminocarbonylamino or $C_1$–$C_7$-alkylaminocarbonylamino group, a $C_1$–$C_7$-alkylmercapto, $C_1$–$C_7$-alkylsulphinyl or $C_1$–$C_7$-alkylsulphonyl group, a nitro, amino, hydroxyl, benzyloxy, $C_1$–$C_7$-alkoxy, $C_1$–$C_7$-alkyl, $C_2$–$C_7$-alkenyl, $C_2$–$C_7$-alkenyloxy, $C_2$–$C_7$-alkynyloxy, cyano-$C_1$–$C_7$-alkoxy, carboxy-$C_1$–$C_7$-alkoxy, phenyl-$C_1$–$C_7$-alkoxy, $C_1$–$C_7$-alkoxycarbonyl-$C_1$–$C_7$-alkoxy, $C_1$–$C_7$-alkylamino, di-$C_1$–$C_7$-alkylamino, trifluoromethyl, cyano, halogen or imidazolyl group or two ortho-positioned substituents $R^4$, $R^5$, together with the C-atoms to which they are attached, form a 5- or 6-membered heterocyclic ring with 1–2 heteroatoms, such as oxygen, nitrogen or sulphur, whereby, in the case of n=0, the benzimidazole ring can be attached in the 4-, 5-, 6- or 7-position with the 2,3-dihydroindol-2-one or, in the case of n=1, the linkage takes place in the 5-, 7-, 8-position or, if $R^3$ does not signify a hydrogen atom, also in the 6-position with the 1,2,3,4-tetrahydroquinolin-2-one, or their physiologically compatible salts and optical isomers, processes for their preparation, as well as medicaments containing these compounds.

The compounds of the general formula I inhibit or reduce not only the erythrocyte aggregation but also the thrombocyte aggregation in low concentrations. On the basis of these properties, these substances are suitable for the treatment of diseases in which, in the pathogenesis, the erythrocyte and thrombocyte aggregation play an important part, such as for example peripheral and cerebral circulatory disturbances, shock states, degenerative blood vessel diseases, rheumatic diseases, various types of ulcers, necrotic processes in tumours, degenerative disturbances of the retina, nerves and muscles or of various skin diseases. In particular, there come into question the treatment of arterial occlusive diseases, ischaemic conditions, venous insufficiency or diabetes mellitus.

Compounds of similar structure as those of the general formula I are known from the Japanese Patent Application JP 86-257720 (Yoshitomi) (C.A. 109(19); 170432 d). It is thereby a question not of benzimidazoles but of imidazopyridines of the general formula II.

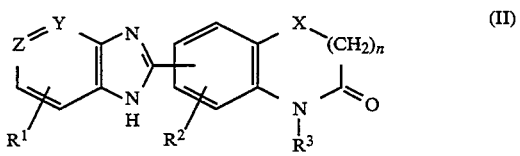

in which, in each case, one of the atoms Y or Z signifies a nitrogen atom, whereas the other represents the group CH and X represents an oxygen or sulphur atom or a possibly substituted methylene group. The compounds of the general formula II act inhibitingly on the platelet aggregation, anti-allergically, inflammation-inhibitingly, sedatively and vasodilatingly.

In European Patent Application EP-A-0,290,153 are described quinoline derivatives which are substituted in the 6-position by a heterobicyclic group. These compounds act positively inotropically.

In the case of the compounds of the formula I according to the invention, the substituents $R^4$, $R^5$ or $R^6$ can, independently of one another, stand in the 4-, 5-, 6- or 7-position of the benzimidazole ring, whereby this can carry, in all, 1–3, preferably 1 or 2 substituents. The alkyl part of these substituents can contain 1–7 carbon atoms, preferably 1–4 carbon atoms and can be straight-chained or branched. Preferred in this meaning are, for example, methanesulphonyloxy, ethanesulphonyloxy, n-propanesulphonyloxy, isopropanesulphonyloxy, trifluoromethane-sulphonyloxy, methylsulphenylmethyl, ethylsulphenylmethyl, n-propylsulphenylmethyl, methylsulphinylmethyl, ethylsulphinylmethyl, n-propylsulphinylmethyl, methylsulphonylmethyl, ethylsulphonylmethyl, n-propylsulphonylmethyl, methanesulphonylamino, ethanesulphonylamino, n-propanesulphonylamino, trifluoromethanesulphonylamino, N-methyl-methanesulphonylamino, N-ethyl-methanesulphonylamino, N-methyl-ethanesulphonylamino, N-ethyl-ethanesulphonylamino, N-isopropyl-ethanesulphonylamino, N-methyl-n-propanesulphonylamino, N-n-propyl-n-propanesulphonylamino, N-methyl-trifluoromethanesulphonylamino, N-ethyl-trifluoromethanesulphonylamino, N-isopropyl-trifluoromethanesulphonylamino, methoxycarbonyl, ethoxycarbonyl, propoxycarbonyl, isopropoxycarbonyl, methylaminocarbonyl, ethylaminocarbonyl, dimethylaminocarbonyl, di-n-propylaminocarbonyl, N-methyl-ethylaminocarbonyl, trifluoromethyl, methylaminosulphonyl, ethylaminosulphonyl, n-propylaminosulphonyl, n-butylaminosulphonyl, n-pentylaminosulphonyl, dimethylaminosulphonyl, diethylaminosulphonyl, di-n-propylaminosulphonyl, diethylaminosulphonyl, di-n-propylaminosulphonyl, N-methyl-isopropylaminosulphonyl, acetylamino, propionylamino, methylcarbonylamino, ethylaminocarbonylamino or propylaminocarbonylamino group a methyl, ethyl, propyl, methoxy, ethoxy, propyloxy, allyloxy, 2-butenyloxy, 3-butenyloxy, 2-pentenyloxy, propargyloxy, 2-butynyloxy, 3-butynyloxy, cyanomethyloxy, cyanoethyloxy, methoxycarbonylmethyloxy, methoxycarbonylethyloxy, methylmercapto, ethylmercapto, methylsulphinyl, ethylsulphinyl, methylsulphonyl or the ethylsulphonyl group.

Especially preferred are for $R^4$ hydrogen, an alkylsulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino group, a carbonyl group substituted by a hydroxyl, alkyl, amino, alkylamino or dialkylamino group or a sulphonyl group substituted by an amino, dialkylamino or morpholino group, whereby each of the above-mentioned alkyl parts can contain preferably 1–4, especially 1 or 2 carbon atoms, a nitro, cyano or alkylaminosulphonyl group with 1–4 carbon atoms, an alkylcarbonylamino, alkylcarbonyloxy, aminocarbonylamino or N-alkylaminocarbonylamino group, an alkylmercapto, alkylsulphinyl or alkylsulphonyl group, whereby each of the above-mentioned alkyl parts can contain preferably 1–4, especially 1 or 2 carbon atoms, an amino, hydroxyl, benzyloxy, dialkylamino, alkyl, alkoxy, alkenyloxy or alkynyloxy group preferably with 1–3 carbon atoms, a phenyl-$C_1$-$C_4$-alkoxyl, cyanomethyloxy or methoxycarbonylmethyloxy group, the trifluoromethyl group, the 1-imidazolyl group or a halogen atom, for $R^5$ hydrogen, a hydroxyl group, an alkyl group with 1–3 carbon atoms, an alkoxy or dialkylamino group with preferably 1–4, especially 1 or 2 carbon atoms in each alkyl part or a halogen atom and $R^6$ hydrogen or an alkoxy group, especially the methoxy group.

If two substituents standing ortho to one another form, with the carbon atoms to which they are attached, heterocyclic 5- or 6-rings, then tricyclic systems result therefrom, such as for example methylenedioxybenzimidazoles, ethylenedioxybenzimidazoles and 1,5-dihydropyrrolo[2,3-f]benzimidazol-6-ones, whereby the last-mentioned radical can be substituted by $C_1$-$C_4$-alkyl groups, especially the methyl group, once or twice. A preferred group in this meaning is the 7,7-dimethyl-1,5-dihydropyrrolo[2,3-f]benzimidazol-6-one radical.

Preferred monosubstituted benzimidazoles are the hydroxyl, $C_1$-$C_7$-alkyl, $C_1$-$C_7$-alkoxy, allyloxy, propargyloxy, cyanomethyloxy, benzyloxy, methoxycarbonyl, halogen, nitro, cyano, aminocarbonyl, methoxycarbonyl, amino, trifluoromethyl, $C_1$-$C_3$-alkylcarbonyloxy, $C_1$-$C_3$-dialkylamino, $C_1$-$C_3$-alkylmercapto, $C_1$-$C_3$-alkylsulphinyl, $C_1$-$C_3$-alkylsulphonyl, $C_1$-$C_3$-alkylsulphonyloxy and the 1-imidazolyl group, whereby the substituent can preferably stand in the 4- or 5-position.

Preferred disubstituted benzimidazoles contain as substituents an alkanesulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino group, a carbonyl group substituted by a hydroxyl, alkoxy, amino, alkylamino or dialkylamino group or a sulphonyl group substituted by an amino, dialkylamino or morpholino group, an alkylaminosulphonyl, alkylcarbonylamino, aminocarbonylamino or N-alkyl-aminocarbonylamino group, a hydroxyl, alkyl, alkoxy, allyloxy, propargyloxy, cyanomethyloxy, methoxycarbonylmethyloxy, cyano, halogen, nitro, amino, dialkylamino, alkylmercapto, alkylsulphinyl, alkylsulphonyl, alkylcarbonyloxy or a 1-imidazolyl group, whereby the two substituents can be the same or different and the above-mentioned alkyl radicals have especially 1–3 C-atoms.

If $R^1$ signifies an alkyl, alkenyl or cycloalkyl group and $R^2$ an alkyl, alkenyl or a carbonyl group substituted by an alkyl, alkoxy, alkylamino or dialkylamino group, then each of the above-mentioned alkyl or alkenyl parts can be straight-chained or branched and contain 1–6 or 2–6 carbon atoms, respectively, and the said cycloalkyl part 3–7 carbon atoms.

Preferred in this meaning is for $R^1$ a hydrogen atom, the methyl, ethyl, isopropyl, 3-pentyl, cyclopentyl or cyclohexyl group. $R^2$ can preferably represent a methyl, ethyl, isopropyl, 3-pentyl, cyano, carboxyl, acetyl, propynyl, methoxycarbonyl, ethoxycarbonyl, aminocarbonyl, methylaminocarbonyl, dimethylaminocarbonyl and hydrazinocarbonyl group.

If $R^1$ and $R^2$, together with the C-atom to which they are attached, form a cycloalkyl ring, then it is thereby preferably a question of the spirocyclopropyl, spirocyclobutyl, spirocyclopentyl and spirocyclohexyl group. If $R^1$ and $R^2$ together form an alkylidene or cycloalkylidene group, the the isopropylidene or cyclohexylidene group is thereby preferred.

The alkyl parts mentioned in the case of $R^3$ can be straight-chained or branched and contain especially 1–4 carbon atoms. $R^3$ preferably signifies a hydrogen atom or a $C_1$-$C_8$-alkyl or $C_2$-$C_6$-alkenyl group. Especially prefered radicals for $R^3$ are the hydrogen atom, the methyl, ethyl, isopropyl, propyl, tert.-butyl, butyl, pentyl, hexyl, heptyl, octyl, allyl, isobutenyl, propargyl, cyclopropyl, cyclobutyl, carboxymethyl, carboxyethyl, carboxypropyl, carboxybutyl, carboxypentyl, ethoxycarbonylmethyl, methoxycarbonylmethyl, methoxycarbonylethyl, methoxycarbonylpropyl, methoxycarbonylbutyl, methoxycarbonylpentyl, ethoxycarbonylethyl, ethoxycarbonylpropyl, ethoxycarbonylbutyl, ethoxycarbonylpentyl, benzyl and the dimethyloxophosphinylmethyl group.

Especially preferred are compounds of the general formula I in which $R^4$ signifies hydrogen, the methanesulphonyloxy, trifluoromethanesulphonyloxy, methanesulphonylamino, trifluoromethanesulphonylamino, methanesulphonylmethylamino, trifluoromethanesulphonylmethylamino, methylsulphinylmethyl, methylsulphonylmethyl, aminocarbonyl, aminosulphonyl, methylaminosulphonyl, dimethylaminosulphonyl, acetylamino, methylmercapto, methylsulphinyl, methylsulphonyl, hydroxyl, allyloxy, methyl, methoxy, propargyloxy, cyanomethyloxy, methoxycarbonylmethyloxy, cyano, chloro, nitro, amino, dimethylamino, trifluoromethyl or the 1-imidazolyl group, $R^5$ hydrogen, the methyl, methoxy, hydroxyl, dimethylamino group or chlorine, $R^6$ is hydrogen or the methoxy group, $R^1$ represents a hydrogen atom or the methyl group and $R^2$ signifies the methyl, ethyl or isopropyl group or $R^1$ and $R^2$, together with the C-atom to which they are attached, represent a spirocyclopentyl ring, $R^3$ signifies a hydrogen atom, the methyl, ethyl, propyl, isopropyl, butyl, isobutenyl, allyl, ethoxycarbonyl or the dimethyloxophosphinylmethyl group.

For the preparation of medicaments, the substances of the general formula I are mixed in per se known manner with suitable pharmaceutical carrier substances, aroma, flavouring and colouring materials and formed, for example, as tablets or dragees or, with the addition of appropriate adjuvants, suspended or dissolved in water or oil, such as e.g. olive oil.

The substances of the general formula I and their salts can be administered enterally or parenterally in liquid or solid form. As injection medium, water is preferably used which contains the additives usual in the case of injection solutions, such as stabilising agents, solubilising agents or buffers.

Such additives are e.g. tartrate and citrate buffers, ethanol, complex formers (such as ethylenediamine-tetraacetic acid and its non-toxic salts) and high molecular polymers (such as liquid polyethylene oxide) for viscosity regulation. Solid carrier materials are e.g. starch, lactose, mannitol, methyl cellulose, talc, highly dispersed silicic acids, high molecular fatty acids (such as stearic acid), gelatine, agar-agar, calcium phosphate, magnesium stearate, animal and vegetable fats and solid high molecular polymers (such as polyethylene glycols). Compositions suitable for oral administration can, if desired, contain flavouring and sweetening materials.

The compounds are usually administered in amounts of 10–1500 mg per day, referred to 75 kg body weight. It is preferred to administer 2–3 times per day 1–2 tablets with an active material content of 5–500 mg. The tablets can also be retarded, whereby only 1–2 tablets with 20–700 mg of active material have to be given once per day. The active material can also be given by injection 1–8 times per day or by continuous infusion, whereby amounts of 10–1000 mg per day normally suffice.

For the conversion of the compounds of the general formula I or of their tautomeric forms into their pharmacologically acceptable salts, one reacts these, preferably in an organic solvent, with the equivalent amount of an inorganic or organic acid, e.g. hydrochloric acid, hydrobromic acid, phosphoric acid, sulphuric acid, acetic acid, citric acid, tartaric acid, maleic acid, fumaric acid, benzoic acid or cyclohexylsulphamic acid.

Compounds of the general formula I are prepared in per se known manner. Especially advantageous is the preparation from the ortho-phenyldiamines of the general formula III and the bicyclic carboxylic acids of the general formula IV:

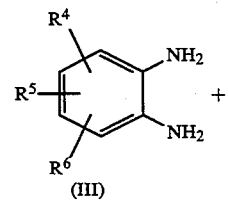

(III)

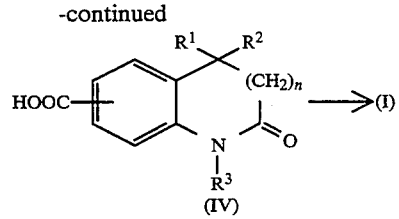

(IV)

In the general formulae III and IV, the substituents $R^1$–$R^6$ and n have the above-given meanings. The compounds of the general formula III are known from the literature (e.g. from EP-A-0,161,632) or are commercially available. The compounds of the general formula IV are described in German Patent Application DE-A-3,818,830 or can be prepared according to the processes there described. Furthermore, the compounds of the formulae III and IV can be prepared according to per se known processes (W. Seidenfaden et al., Methoden der organischen Chemie, Houben-Weyl, Vol. X/1, p. 461, Thieme Verlag Stuttgart 1971).

For the preparation of the compounds of the formula I, the compounds III and IV are reacted with a water-removing agent. As such, in the first place, there comes into consideration polyphosphoric acid, advantageously with the addition of diphosphorus pentoxide. One works at temperatures between 100° and 200° C. In the case of aqueous working up, a phosphate of the desired compound usually precipitates out. One obtains the free base therefrom by alkalisation, preferably with aqueous ammonia. According to this method, there can be reacted not only the acids of the general formula IV but also derivatives thereof, such as esters (ethyl or methyl esters), amides and the corresponding nitriles. The reaction can also be carried out completely without solvents if one works in the melt. If, instead of the acids of the general formula IV, one uses their acid chlorides, which are obtained from the acids by reaction with thionyl chloride, phosphoryl chloride or phosphorus pentachloride, then the reaction with the ortho-phenylenediamines of the general formula III takes place in inert solvents, preferably dichloromethane or pyridine, and the cyclisation in a solvent or solvent mixture, such as ethanol, isopropanol, glacial acetic acid, glycol, sulfolane or dimethylformamide, at temperatures between 0° C. and 250° C. but preferably at the boiling temperature of the solvent, possibly in the presence of a condensation agent, such as phosphoryl chloride, thionyl chloride, p-toluenesulphonic acid, hydrochloric acid, sulphuric acid, phosphoric acid, polyphosphoric acid, or also in the presence of a base, such as sodium hydroxide, potassium methylate.

A further preferred process for the preparation of the compounds of the general formula I consists in the reductive ring closure of N-(ortho-nitrophenyl)-amides of the general formula V

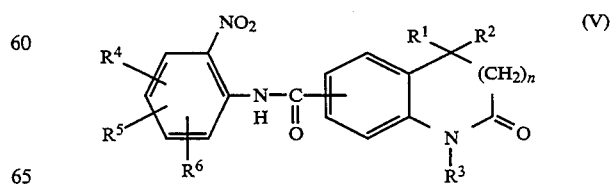

(V)

in which the substituents $R^1$–$R^6$ have the above-given meanings. The reduction of the nitro group is preferably carried out in a solvent, such as water, ethanol, glacial acetic acid, acetic acid ethyl ester or dimethylformamide, with hydrogen in the presence of a catalyst, such as Raney nickel, platinum or palladium, or with metals, such as iron, tin or zinc in the presence of an acid, with salts, such as iron (II) sulphate, tin (II) chloride, sodium sulphate, sodium hydrogen sulphide or with hydrazine in the presence of Raney nickel at temperatures between 0° and 250° C., preferably at room temperature. Under the reaction conditions, the ring closure to the compounds of the general formula I usually takes place. If desired, the reaction can be completed with the use of a water-removing agent such as is described above for the reaction of the compounds of the general formulae III and IV.

One obtains the compounds of the general formula V by reaction of the ortho-nitroanilines of the general formula VI

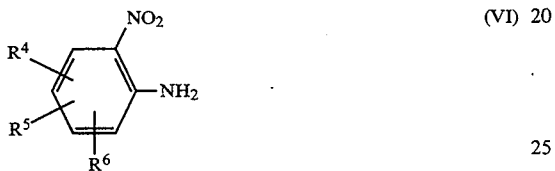

in which $R^4$–$R^6$ have the above-given meanings, with the acids of the general formula IV or their activated derivatives, such as e.g. acid chlorides. These reactions are described in DE-A-3,818,830.

A further preferred process for the preparation of the compounds of the general formula V consists in the nitration of compounds of the general formula VII

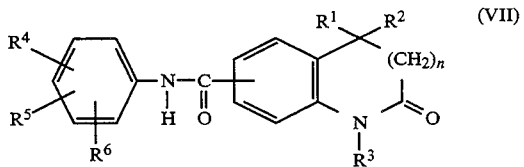

in which $R^1$–$R^6$ and n have the above-given meanings One preferably carries out the nitration with nitric acid in sulphuric acid at temperatures between −20° C. and +50° C. It can also be carried out without sulphuric acid or, in place thereof, in water, glacial acetic acid or acetic anhydride or with $N_2O_5$ in $CCl_4$ in the presence of $P_2O_5$. As nitration agents, there can also serve anhydrides, such as acetyl nitrate, or nitryl halides with $FeCl_3$, methyl nitrate with $BF_3$ or sodium salts, such as $NO_2BF_4$, $NO_2PF_6$ or $NO_2CF_3SO_3$. For the nitration, there can also be used a mixture of nitric acid and nitrous acid which serves as $N_2O_4$ provider.

Compounds of the general formula I can also be subsequently converted into other compounds of the general formula I.

a) The subsequent conversion concerns compounds of the general formula I, in which one of the substituents $R^4$, $R^5$ or $R^6$ signifies a benzyloxy substituent, into those in which $R^4$, $R^5$ or $R^6$ signifies a hydroxyl group. This conversion takes place by reduction by means of hydrogen in the presence of a catalyst, such as palladium or platinum, or by sodium in liquid ammonia.

b) The subsequent conversion also concerns the alkylation of compounds of the general formula I, in which $R^4$, $R^5$ or $R^6$ signifies a hydroxyl group, into those in which $R^4$, $R^5$ or $R^6$ signifies a benzyloxy, alkoxy, a benzyloxy, alkoxy, alkenyloxy, alkynyloxy, cyanoalkoxy, carboxyalkoxy, phenylalkoxy or alkoxycarbonylalkoxy group. This alkylation is preferably carried put in a solvent, such as acetone, ether, benzene, toluene or dimethylformamide, at temperatures between −30° C. and +100° C., preferably between room temperature and 100° C., in the presence of a base, such as potassium hydroxide and of an alkylation agent, such as alkyl halides or alkyl sulphates.

c) The subsequent conversion also concerns the preparation of compounds of the general formula I, in which $R^4$ represents an alkylsulphinyl or alkylsulphonyl group, by subsequent oxidation of a compound in which $R^4$ is an alkylmercapto group. The oxidation is preferably carried out in a solvent or solvent mixture, e.g. water, water/pyridine, acetone, glacial acetic acid, dilute sulphuric acid or trifluoroacetic acid, depending upon the oxidation agent used, expediently at temperatures between −80° C. and 100° C.

For the preparation of an alkylsulphinyl compound of the general formula I, the oxidation is expediently carried out with one equivalent of the oxidation agent used, e.g. with hydrogen peroxide in glacial acetic acid, trifluoroacetic acid or formic acid, at 0° to 20° C. or in acetone at 0° to 60° C., with a peracid, such as performic acid, in glacial acetic acid or trifluoroacetic acid, at 0° to 50° C. or with m-chloroperbenzoic acid in methylene chloride or chloroform at −20° C. to 60° C., with sodium metaperiodate in aqueous methanol or ethanol at −15° C. to 25° C., with bromine in glacial acetic acid or aqueous acetic acid, with N-bromo-succinimide in ethanol, with tert.-butyl hypochlorite in methanol at −80° C. to −30° C., with iodobenzodichloride in aqueous pyridine at 0° to 50° C., with nitric acid in glacial acetic acid at 0° to 20° C., with chromic acid in glacial acetic acid or in acetone at 0° to 20° C. and with sulphuryl chloride in methylene chloride at −70° C., the hereby obtained thioether-chlorine complex being expediently hydrolysed with aqueous ethanol.

For the preparation of an alkylsulphonyl compound of the general formula I, the oxidation is expediently carried out with two or more equivalents of the oxidation agent used, e.g. hydrogen peroxide in glacial acetic acid, trifluoroacetic acid or in formic acid at 20° to 100° C. or in acetone at 0° to 60° C.; with a per acid, such as performic acid or m-chloroperbenzoic acid in glacial acetic acid, trifluoroacetic between 0° and 60° C., with nitric acid in glacial acetic acid at 0° to 20° C.

d) The subsequent conversion also concerns the preparation of compounds of the general formula I, in which $R^4$ represents an alkanesulphonyloxy, trifluoromethanesulphonyloxy, alkanesulphonylamino or trifluoromethanesulphonylamino group, by the subsequent reaction of a compound in which $R^4$ is a hydroxyl group with a sulphonic acid of the general formula VIII:

in which $R^7$ represents an alkyl group or the trifluoromethyl group, in the presence of a water-removing agent and/or of an agent activating the acid or the amine or with their reactive derivatives.

The reaction is expediently carried out in a solvent or solvent mixture, such as methylene chloride, ether, tetrahydrofuran, dioxane or benzene, possibly in the presence of an acid-binding agent, such as sodium carbonate, triethylamine or pyridine, whereby the last two can simultaneously also be used as solvent, in the presence of an agent activating the acid or removing water, such as thionyl chloride or phosphorus pentachloride, but preferably with a reactive derivative of a compound of the general formula VIII, e.g. with its anhydride or halide, such as methanesulphonic acid chloride or ethanesulphonic acid chloride, at temperatures between 0° and 100° C., preferably at temperatures between room temperature and 50° C.

e) The subsequent conversion also concerns the preparation of compounds of the general formula I, in which $R^4$ represents a carbonyl group substituted by an amino, alkylamino or dialkylamino group, by the subsequent reaction of a compound in which $R^4$ represents a carboxyl group, or a reactive derivative hereof, such as e.g. ester or acid chloride, with an amine of the general formula IX

$$HNR^8R^9 \qquad (IX)$$

in which $R^8$ and $R^9$, which can be the same or different, represent hydrogen atoms or alkyl groups, or with a reactive derivative hereof if $R^4$ represents the carboxyl group. The reaction is expediently carried out in a solvent, such as methylene chloride, ethanol, chloroform, carbon tetrachloride, ether, tetrahydrofuran, dioxane, benzene, toluene, acetonitrile or dimethylformamide, possibly in the presence of an agent activating the acid or of a water-removing agent, e.g. in the presence of chloroformic acid ethyl ester, thionyl chloride, phosphorus trichloride, phosphorus pentoxide, N,N'-dicyclohexylcarbodiimide/N-hydroxysuccinimide, N,N'-carbonyldiimidazole or N,N'-thionyldiimidazole or triphenylphosphine/carbon tetrachloride, or of an agent activating the amino group, e.g. phosphorus trichloride, and possibly in the presence of an inorganic base, such as sodium carbonate, or of a tertiary organic base, such as triethylamine or pyridine, which can simultaneously serve as solvent, at temperatures between −25° and 250° C., but preferably at temperatures between −10° C. and the boiling point of the solvent used, furthermore, water formed during the reaction can be removed by azeotropic distillation, e.g. by heating with toluene on a water separator, or by addition of a drying agent, such as magnesium sulphate or molecular sieve.

However, the reaction is carried out especially advantageously with an appropriate halide, e.g. the carboxylic acid or sulphonic acid chloride, and an appropriate amine, whereby this can simultaneously serve as solvent, at temperatures between 0° and 50° C.

f) The subsequent conversion also concerns the reaction of compounds of the general formula I, in which $R^2$ signifies the alkoxycarbonyl group, to give compounds of the general formula I, in which $R^2$ signifies the hydrazinocarbonyl group. For this purpose, one reacts in a solvent, such as ethanol, methanol or glacial acetic acid, with a small excess of hydrazine hydrate at temperatures between room temperature and the boiling point of the solvent.

g) The subsequent conversion also concerns the alkylation of compounds of the general formula I, in which $R^3$ signifies a hydrogen atom, to give those in which $R^3$ signifies an alkyl, alkenyl, alkynyl, cycloalkyl, benzyl, carboxyalkyl, alkoxycarbonylalkyl or the dimethyloxophosphinylmethyl group. These alkylations are preferably carried out in a solvent, such as acetone, methyl ethyl ketone, ether, benzene, toluene, xylene or dimethylformamide, at temperatures between −30° C. and the boiling point of the solvent, preferably at 0° C.–80° C., in the presence of a base, such as sodium hydride, sodium hydroxide or potassium carbonate. In the case of the use of two-phase mixtures, such as perhaps toluene/sodium hydroxide or in sodium hydroxide solution, the use of a phase transfer catalyst is of advantage.

In the meaning of the present invention, by way of example the following compounds are mentioned:

1. 2-(3-methyl-2,3-dihydro-2-oxo-(1H)-6-indolyl)-benzimidazole
2. 2-(3,3-diethyl-2,3-dihydro-2-oxo-(1H)-6-indolyl)-benzimidazole
3. 2-(3-isopropyl-2,3-dihydro-2-oxo-(1H)-6-indolyl)-benzimidazole
4. 2-(3-methyl-3-ethoxycarbonyl-2,3-dihydro-2-oxo-(1H)-6-indolyl)-benzimidazole
5. 2-(2',3'-dihydro-2'-oxo-(1'H)-spiro/cyclopropane-1,3'-indol/-6-yl)-benzimidazole
6. 2-(2',3'-dihydro-2'-oxo-(1'H)-spiro/cyclobutane-1,3'-indol/-6-yl)-benzimidazole
7. 2-(2',3-dihydro-2'-oxo-(1'H)-spiro/cyclohexane-1,3'-indol/-6-yl)-benzimidazole
8. 2-(3,3-dimethyl-2,3-dihydro-2-oxo-(1H)-6-indolyl)-5-trifluoromethylbenzimidazole
9. 2-(3,3-dimethyl-2,3-dihydro-2-oxo-(1H)-6-indolyl)-5-methylbenzimidazole
10. 2-(3,3-dimethyl-2,3-dihydro-2-oxo-(1H)-6-indolyl)-5-fluorobenzimidazole
11. 2-(3-methyl-2,3-dihydro-2-oxo-(1H)-5-indolyl)-benzimidazole
12. 2-(3,3-diethyl-2,3-dihydro-2-oxo-(1H)-5-indolyl)-benzimidazole
13. 2-(3-isopropyl-2,3-dihydro-2-oxo-(1H)-5-indolyl)-benzimidazole
14. 2-(3-methyl-3-ethoxycarbonyl-2,3-dihydro-2-oxo-(1H)-5-indolyl)-benzimidazole
15. 2-(2',3'-dihydro-2'-oxo-(1IH)-spiro[cyclopropane-1,3'-indol]-yl)-benzimidazole
16. 2-(2',3'-dihydro-2'-oxo-(1'H)-spiro[cyclobutane-1,3'-indol]-5-yl)-benzimidazole
17. 2-(2',3-dihydro-2'-oxo-(1IH)-spiro[cyclohexane-1,3'-indol]-5-yl)-benzimidazole
18. 2-(3,3-dimethyl-2,3-dihydro-2-oxo-(1H)-5-indolyl)-5-trifluoromethylbenzimidazole
19. 2-(3,3-dimethyl-2,3-dihydro-2-oxo-(1H)-5-indolyl)-5-methylbenzimidazole
20. 2-(3,3-dimethyl-2,3-dihydro-2-oxo-(1H)-5-indolyl)-5-fluorobenzimidazole
21. 2-(4,4-dimethyl-1,2,3,4-tetrahydro-2-oxo-7-quinolinyl)-5-methoxybenzimidazole
22. 2-(4,4-dimethyl-1,2,3,4-tetrahydro-2-oxo-7-quinolinyl)-4-methoxybenzimidazole
23. 2-(4,4-dimethyl-1,2,3,4-tetrahydro-2-oxo-7-quinolinyl)-5-chlorobenzimidazole
24. 2-(4,4-dimethyl-1,2,3,4-tetrahydro-2-oxo-7-quinolinyl)-5-fluorobenzimidazole
25. 2-(4,4-dimethyl-1,2,3,4-tetrahydro-2-oxo-7-quinolinyl)-5-methylbenzimidazole
26. 2-(4,4-dimethyl-1,2,3,4-tetrahydro-2-oxo-7-quinolinyl)-5-trifluoromethylbenzmidazole 27. 2-(1,4,4-trimethyl-1,2,3,4-tetrahydro-2-oxo-6-quinolinyl)-5-methoxybenzimidazole
28. 2-(1,4,4-trimethyl-1,2,3,4-tetrahydro-2-oxo-6-quinolinyl)-4-methoxybenzimidazole
29. 2-(1,4,4-trimethyl-1,2,3,4-tetrahydro-2-oxo-6-quinolinyl)-5-chlorobenzimidazole
30. 2-(1,4,4-trimethyl-1,2,3,4-tetrahydro-2-oxo-6-quinolinyl)-5-fluorobenzimidazole
31. 2-(1,4,4-trimethyl-1,2,3,4-tetrahydro-2-oxo-6-quinolinyl)-5-methylbenzimidazole
32. 2-(1,4,4-trimethyl-1,2,3,4-tetrahydro-2-oxo-6-quinolinyl)-5-trifluoromethylbenzimidazole
33. 2-(3,3-dimethyl-1-ethyl-2,3-dihydro-2-oxo-(1H)-6-indolyl)-5-methoxybenzimidazole
34. 2-(3,3-dimethyl-1-ethyl-2,3-dihydro-2-oxo-(1H)-6-indolyl)-4-methoxybenzimidazole
35. 2-(3,3-dimethyl-1-ethyl-2,3-dihydro-2-oxo-(1H)-6-indolyl)-5-trifluoromethylbenzimidazole
36. 2-(3,3-dimethyl-1-ethyl-2,3-dihydro-2-oxo-(1H)-6-indolyl)-5-methylbenzimidazole
37. 2-(3,3-dimethyl-1-ethyl-2,3-dihydro-2-oxo-(1H)-6-indolyl)-5-fluorobenzimidazole
38. 2-(3,3-dimethyl-1-allyl-2,3-dihydro-2-oxo-(1H)-6-indolyl)-5-methoxybenzimidazole
39. 2-(3,3-dimethyl-1-allyl-2,3-dihydro-2-oxo-(1H)-6-indolyl)-4-methoxybenzimidazole
40. 2-(3,3-dimethyl-1-allyl-2,3-dihydro-2-oxo-(1H)-6-indolyl)-5-trifluoromethylbenzimidazole
41. 2-(3,3-dimethyl-1-allyl-2,3-dihydro-2oxo-(1H)-6-indolyl)-5-methylbenzimidazole
42. 2-(3,3-dimethyl-1-allyl-2,3-dihydro-2-oxo-(1H)-6-indolyl)-5-fluorobenzimidazole
43. 2-(3,3-dimethyl-1-dimethyloxophosphinylmethyl-2,3-dihydro-2-oxo-(1H)-6-indolyl)-5-methoxybenzimidazole
44. 2-(3,3-dimethyl-1-dimethyloxophosphinylmethyl-2,3-dihydro-2-oxo-(1H)-6-indolyl)-4-methoxybenzimidazole
45. 2-(3,3-dimethyl-1-dimethyloxophosphinylmethyl-2,3-dihydro-2-oxo-(1H)-6-indolyl)-5-trifluoromethylbenzimidazole
46. 2-(3,3-dimethyl-1-dimethyloxophosphinylmethyl-2,3-dihydro-2-oxo-(1H)-6-indolyl)-5-methylbenzimidazole
47. 2-(3,3-dimethyl-1-dimethyloxophosphinylmethyl-2,3-dihydro-2-oxo-(1H)-6-indolyl)-5-fluorobenzimidazole
48. 2-(3,3-dimethyl-1-methyl-2,3-dihydro-2-oxo-(1H)-6-indolyl)-5-methoxybenzimidazole
49. 2-(3,3-dimethyl-1-methyl-2,3-dihydro-2-oxo-(1H)-6-indolyl)-4-methoxybenzimidazole
50. 2-(3,3-dimethyl-1-methyl-2,3-dihydro-2-oxo-(1H)-6-indolyl)-5-trifluoromethylbenzimidazole
51. 2-(3,3-dimethyl-1-methyl-2,3-dihydro-2-oxo-(1H)-6-indolyl)-5-methylbenzimidazole
52. 2-(3,3-dimethyl-1-methyl-2,3-dihydro-2-oxo-(1H)-6-indolyl)-5-fluorobenzimidazole

EXAMPLE 1

2-(4,4-Dimethyl-1,2,3,4-tetrahydro-2-oxo-7-quinolinyl)-benzimidazole

One stirs ortho-phenylenediamine (1.30 g, 12.0 mmol) and 4,4-dimethyl-1,2,3,4-tetrahydro-2-oxo-7-quinolinecarboxylic acid (2.60 g, 12.0 mmol; preparation see DE-A-3,818,830) in a mixture of polyphosphoric acid (50 g) and diphosphorus pentoxide (10 g) for 3 hours at 160° C. One allows to cool to 80°–90° C., carefully adds ice and water thereto and filters off the precipitate with suction. One takes up in water (200 ml), adds conc. ammonia thereto, filters off with suction, dissolves the residue in hot ethanol, filters and allows to crystallise. One dries the colourless crystals at 120° C. in a vacuum and obtains 1.30 g (37%) of the title compound with the m.p. 314°–316° C. which, per mole, still has adhering a half mol of water.

EXAMPLE 2

2-(4,4-Dimethyl-1-ethyl-1,2,3,4-tetrahydro-2-oxo-7-quinolinyl)-benzimidazole

From ortho-phenylenediamine (0.7 g, 6.7 mmol) and 4,4-dimethyl-1-ethyl-1,2,3,4-tetrahydro-2-oxo-7-quinolinecarboxylic acid (1.6 g, 6.5 mmol), polyphosphoric acid (30 g) and diphosphorus pentoxide (7 g) one obtains, according to the procedure of Example 1, 1.3 g (62%) of the title compound with the m.p.=257°–259° C.

One prepared 4,4-dimethyl-1-ethyl-1,2,3,4-tetrahydro-2-oxo-7-quinolinecarboxylic acid analogously to the procedure for 4,4-dimethyl-1,2,3,4-tetrahydro-2-oxo-7-quinolinecarboxylic acid (DE-A-3,818,830) as follows: one stirred 4,4-dimethyl-1,2,3,4-tetrahydro-2-oxo-7-quinolinecarbonitrile (2.0 g, 10.0 mmol), iodoethane (1 ml, 12.0 mmol) and potassium carbonate (1.70 g, 12.0 mmol) for one hour at 60° C., again added iodoethane (2 ml, 24 mmol) and potassium carbonate (2.5 g, 25 mmol) thereto and stirred for one hour at 60° C. One allowed to cool to room temperature, stirred the solution into water, filtered off the precipitate with suction and dried in a vacuum. One obtains 4,4-dimethyl-1-ethyl-1,2,3,4-tetrahydro-2-oxo-7-quinolinecarbonitrile (1.1 g, 48%) with the m.p.=120°–121° C.

One stirred 4,4-dimethyl-1-ethyl-1,2,3,4-tetrahydro-2-oxo-7-quinolinecarbonitrile (3.70 g, 16.2 mmol) for 2 h in 2N KOH (100 ml) at 80° C. One acidified with 2N HCl, filtered off the precipitate with suction, dried in the air and obtained 4,4-dimethyl-1-ethyl-1,2,3,4-tetrahydro-2-oxo-7-quinoline-carboxylic acid (3.8 g, 95%) with the m.p.=202°–204° C.

EXAMPLE 3

2-(3,3-Dimethyl-2,3-dihydro-2-oxo-(1H)-6-indolyl)benzimidazole

One heated 3,3-dimethyl-2,3-dihydro-2-oxo-(1H)-6-indolecarbonitrile (2.6 g, preparation described in DE-A-3,818,830) and ortho-phenylenediamine (2.6 g) in polyphosphoric acid for 6 h at 160° C. One allowed to cool to 80°–90° C., added ice thereto, diluted with water to a volume of 1.2 l and neutralised with conc. ammonia. One extracted with a mixture of dichloromethane:methanol=10:1, removed the solvent in a vacuum and purified the residue column chromatographically (silica gel 60, dichloromethane:methanol. ammonia=20:1). One obtained 0.4 g of grey crystals which one recrystallised from ethanol/water. One obtained 195 mg of the title compound with the m.p. 326°–330° C.

EXAMPLE 4

2-(3,3-Dimethyl-1-ethyl-2,3-dihydro-2-oxo-(1H)-6-indolyl)-benzimidazole

According to the procedure from Example 1, one obtained from ortho-phenylenediamine (1.5 g, 14.0 mmol), 3,3-dimethyl-1-ethyl-2,3-dihydro-2-oxo-(1H)-6-indolecarboxylic acid (3.30 g, 14.0 mmol), polyphosphoric acid (50 g) and diphosphorus pentoxide (10 g)

2.80 g (65%) of the title compound with the m.p. 261°–263° C.

EXAMPLE 5

2-(3,3-Dimethyl-2,3-dihydro-2-oxo-(1H)-5-indolyl)-benzimidazole with the m.p. 296°–298° C. is obtained in 84% yield analogously to Example 1 from ortho-phenylenediamine (1.62 g, 15.4 mmol), 3,3-dimethyl-2,3-dihydro-2-oxo-(1H)-5-indolecarboxylic acid (3.08 g, 15.4 mmol), prepared according to R. F. Moore, S.G.P. Plant., J. Chem. Soc. 1951, 3475), polyphosphoric acid (63.5 g) and diphosphorus pentoxide (12.5 g).

EXAMPLE 6

2-(3,3-Dimethyl-2,3-dihydro-2-oxo-(1H)-6-indolyl)-7,7-dimethyl-1,7-dihydro-(5H)-pyrrolo/2,3-f/benzimidazol-6-one One reacts together 5,6-diamino-3,3-dimethyl-2,3-dihydro-2-oxo-(1H)-indole (1.90 g, 10.0 mmol, preparation described in EP-A-0,161,632) and 3,3-dimethyl-2,3-dihydro-2-oxo-(1H)-6-indolecarboxylic acid (2.1 g, 10 mmol) as described in Example 1 and obtains 1.0 g (28%) of the title compound with the m.p. 266°–268° C. which, per mol of substance, still has adhering one mol of water.

EXAMPLE 7

2-(3,3-Dimethyl-2,3-dihydro-2-oxo-(1H)-6-indolyl)-5-chlorobenzimidazole with the m.p. 287°–289° C. is obtained in 61% yield according to the procedure of Example 1 from 4-chloro-ortho-phenylenediamine and 3,3-dimethyl-2,3-dihydro-2-oxo-(1H)-6-indolecarboxylic acid.

EXAMPLE 8

2-(3,3-Dimethyl-1-dimethyloxophosphinylmethyl-2,3-dihydro-2-oxo-(1H)-5-indolyl)-benzimidazole One stirred 2-(3,3-dimethyl-2,3-dihydro-2-oxo-(1H)-5-indolyl)-benzimidazole (2.00 g, 7.20 mmol), chloromethyldimethylphosphane oxide (1.82 g, 14.4 mmol) and potassium carbonate (1.99 g, 14.4 mmol) for 12 h at 90° C. One allowed to cool to room temperature, stirred into water (100 ml) and applied the aqueous phase to a chromatography column (40×250 mm, Lichropep ® RP-18, grain size 15–25 μm, firm Merck, Darmstadt). Salts were removed by elution with water, the substance was separated with a mixture of methanol/water (60:40 v/v). One removed the elution agent in a vacuum and obtained 1.9 g (73%) of the title compound with the m.p. 317°–321° C.

EXAMPLE 9

2-(3,3-Dimethyl-2,3-dihydro-2-oxo-(1H)-6-indolyl)-5-methoxybenzimidazole

One stirred 3,3-dimethyl-2,3-dihydro-2-oxo-(1H)-6-indolecarboxylic acid (60 g) and thionyl chloride for 16 h at room temperature, removed excess thionyl chloride in a vacuum and added the brown residue portionwise to a suspension of 4-methoxy-ortho-phenylenediamine (0.61 g) in dichloromethane (20 ml) which contained triethylamine (1.4 ml). One removed the solvent in a vacuum, added thereto ethanol (10 ml) and conc. hydrochloric acid (2 ml) and heated to the boil under reflux for 1 h. One removed the solvent in a vacuum and purified the residue (0.65 g) column chromatographically (silica gel, dichloromethane/methanol. ammonia). After evaporation of the appropriate fractions, one obtained 330 mg of the title compound with the m.p. 85°–90° C.

EXAMPLE 10

2-(2′,3′-Dihydro-2′-oxo-(1′H)-spiro[cyclopentane-1,3′-indol]-6-yl)-benzimidazole According to the process described in Example 9, one obtained from 2′,3′-dihydro-2′-oxo-(1IH)-spirocyclpentane-1,3′-indole-6′-carboxylic acid (2 g, preparation described in DE-A-3,818,830), thionyl chloride (10 ml), ortho-phenyldiamine (1.43 g), dichloromethane (50 ml), triethylamine (3.4 ml), ethanol (20 ml) and conc. hydrochloric acid (2 ml) the title compound (0.46 g) with the m.p. 165°–170° C.

EXAMPLE 11

2-(4,4-Dimethyl-1-dimethyloxophosphinylmethyl-1,2,3,4-tetrahydro-2-oxo-7-quinolinyl)-benzimidazole One stirred ortho-phenylenediamine (0.9 g, 7.8 mmol) and 4,4-dimethyl-1-dimethyloxophosphinylmethyl-1,2,3,4-tetrahydro-2-oxo-7-quinolinecarboxylic acid (2.4 g, 7.8 mmol) in a mixture of polyphosphoric acid (50 g) and diphosphorus pentoxide (10 g) for three hours at 160° C. One allowed to cool to 80°–90° C., added water thereto and extracted three times with n-butanol. One extracted the butanol phase successively with aqueous ammonia and water and dried it over sodium sulphate. One filtered, removed the solvent in a vacuum, recrystallised the residue from ethyl acetate and obtained 0.8 g (27%) of the title compound with the m.p. 380°–384° C.

One obtained the precursor as follows: One stirred 4,4-dimethyl-1,2,3,4-tetrahydro-2-oxo-7-quinolinecarbonitrile (7.5 g, 37.5 mmol), chloromethyldimethylphosphane oxide (9.5 g, 75 mmol) and potassium carbonate (10.4 g, 75 mmol) for 2.5 h at 110° C. in dimethylformamide (100 ml), poured it on to water, filtered off the precipitate with suction, dried in a vacuum and obtained 4,4-dimethyl-1-dimethyloxophosphinylmethyl-1,2,3,4-tetrahydro-7-quinoline carbonitrile (8.5 g, 75%) with the m.p. 183°–186° C. One stirred this compound (8.2 g, 28 mmol) for 2 h at 80° C. in 2N KOH (150 ml). One acidified with 2N HCl, filtered off the precipitate with suction, dried in the air and obtained 4,4-dimethyl-1-dimethyloxophosphinylmethyl-1,2,3,4-tetrahydro-2-oxo-7-quinoline carboxylic acid (7.7 g, 88%) with the m.p. 235°–238° C.

EXAMPLE 12

2-(3,3-Dimethyl-1-ethyl-2,3-dihydro-2-oxo-(1H)-5-indolyl)-benzimidazole with the m.p. 263°–265° C. is obtained in 90% yield analogously to Example 5.

EXAMPLE 13

2-(3,3-Dimethyl-1-allyl-2,3-dihydro-2-oxo-(1H)-6-indolyl)-benzimidazole with the m.p. 197°–200° C. is obtained in 17% yield analogously to Example 4.

EXAMPLE 14

2-(3,3-Dimethyl-1-dimethyloxophosphinylmethyl-2,3-dihydro-2-oxo-(1H)-6-indolyl)-benzimidazole with the m.p. 304°–307° C. is obtained in 39% yield analogously to Example 11 from ortho-phenylenediamine and 3,3-dimethyl-1-dimethyloxophosphinylmethyl-2,3-dihydro-2-oxo-(1H)-indole-6-carboxylic acid (m.p. 300°–303° C.) which one obtains analogously to Example 11 in 82% yield from 3,3-dimethyl-1-dimethyloxophosphinylmethyl-2,3-dihydro-2-oxo-(1H)-indole-6-carbonitrile (m.p. 169°-170° C.) which was also obtained analogously to Example 11 in 81% yield from 3,3-dimethyl-2,3-dihydro-2-oxo-(1H)-indole-6-carbonitrile.

EXAMPLE 15

2-(3,3-Dimethyl-2,3-dihydro-2-oxo-(1H)-6-indolyl)-4-methoxybenzimidazole with the m.p. 222°-225° C. is obtained in 45% yield analogously to Example 9 by reaction with 3-methyoxy-1,2-diaminobenzene.

EXAMPLE 16

2-(3,3-Dimethyl-2,3-dihydro-2-oxo-(1H)-6-indolyl)-5-trifluoromethylbenzimidazole with the m.p. 268°-270° C. is obtained in 33% yield analogously to Example 9 by reaction with 4-trifluoromethyl-1,2-diaminobenzene.

EXAMPLE 17

2-(3,3-Dimethyl-2,3-dihydro-2-oxo-(1H)-6-indolyl)-5-fluorobenzimidazole with the m.p. 329°-332° C. is obtained in 30% yield analogously to Example 4 by reaction with 4-fluoro-1,2-diaminobenzene.

EXAMPLE 18

2-(1,3,3-Trimethyl-2,3-dihydro-2-oxo-(1H)-6-indolyl)-benzimidazole with the m.p. 266°-269° C. is obtained in 80% yield analogously to Example 4 by reaction with ortho-phenylenediamine with 1,3,3-trimethyl-2,3-dihydro-2-oxo-(1H)-6-indolecarboxylic acid.

One prepares the precursor as follows: One mixes 3,3-dimethyl-2,3-dihydro-2-oxo-(1H)-indole-carbonitrile (28 g, 154 mmol) and concentrated caustic soda lye (56 ml) in a mixture of tetrahydrofuran (55 ml) and toluene (70 ml) dropwise with iodomethane (14.1 ml, 225 mmol), whereby one keeps the temperature at 45° C. One stirred for 2 h at this temperature, poured on to ice water (500 ml), filtered off the precipitated product with suction and washed with water. One obtained 22.3 g (74%) 1,3,3-trimethyl-2,3-dihydro-2-oxo-(1H)-6-indole-carbonitrile with the m.p. 143°-145° C. One stirred this compound (19 g, 95 mmol) in 2N KOH (700 ml) for 2 h at 80° C. One acidified with 6N HCl, filtered off the precipitated product with suction and washed with water. One obtained 20.1 g (97%) 1,3,3-trimethyl-2,3-dihydro-2-oxo-(1H)-6-indole-carboxylic acid with the m.p. 253°-255° C.

EXAMPLE 19

2-(1,3,3-Trimethyl-2,3-dihydro-2-oxo-(1H)-5-indolyl)-benzimidazole with the m.p. 243°-245° C. is obtained analogously to Example 4 by reaction of 1,3,3trimethyl-2,3-dihydro-2-oxo-(1H)-5-indole-carboxylic acid with ortho-phenylenediamine.

EXAMPLE 20

2-(3,3-Dimethyl-2,3-dihydro-2-oxo-(1H)-6indolyl-5-methylbenzimidazole with the m.p. 256°-259° C. is obtained in 46% yield analogously to Example 4.

EXAMPLE 21

Haemorheological findings

Determination of the erythrocyte aggregation as parameter for the haemorheology: The determination took place with the mini-erythrocyte aggregometer of the form Myrenne, Roetgen[1]. As measure, this device gives a non-dimensional index which increases with increasing aggregation tendency.

The investigations were carried out with the human blood of healthy donors. The blood adjusted to a haemocrit of 45% was incubated with the control solution or the substance solutions. Subsequently, the erythrocyte aggregation was measured. Per substance, two experiments were carried out with the blood of different donors. There was calculated the difference of the aggregation indices between the initial value of the control solution and the values with the substance solution. These values are listed in the following Table.

Venoruton ®, a mixture of different O-($\beta$-hydroxyethyl)-rutosides, is said to inhibit[2] the tendency of the erythrocyte aggregation. In the above experimental procedure, in the case of a comparable concentration of $1.7 \times 10^{-5}$M, it brings about a change of the aggregation index of only $-0.4$ units. Even in the case of a concentration of $1.7 \times 10^{-3}$M, the change only amounts to $-3.9 \pm 0.9$. In comparison with Venoruton ®, the said substances inhibit the erythrocyte aggregation considerably more strongly.

Literature

1) Kiesewetter, H, et al., Das Mini-Erythrozyten-Aggregometer: Ein neues Gerät zur schnellen Quantifizierung des Ausmasses der Erythrozyten-Aggregation (The mini-erythrocyte aggregometer: A new apparatus for the rapid quantification of the extent of the erythrocyte aggregation), Biomed. Technik 27 (1982), issue 9, p. 209–213.

2) Schmid-Schönbein, H. et al., Effect of O-($\beta$-hydroxyethyl)-rutosides on the microrheology of human blood under defined flow conditions, VASA 4 (1975) 263–270.

TABLE

| Difference of the aggregation indices ($A_2-A_1$) | |
|---|---|
| compound | $A_2-A_1$ |
| Example 1 | $-8.3$ |
| Example 2 | $-8.1$ |
| Example 7 | $-7.8$ |
| Example 8 | $-7.0$ |
| Example 17 | $-8.2$ |

We claim:
1. Bicyclobenzimidazoles of formula I

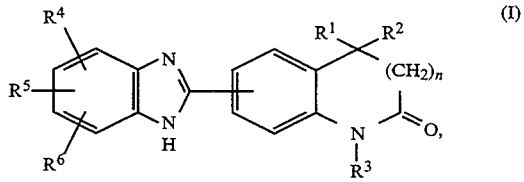

wherein
$R^1$ is hydrogen, $C_1$–$C_6$-alkyl, $C_2$–$C_6$-alkenyl or $C_3$–$C_7$-cycloalkyl,
$R^2$ is $C_1$–$C_6$-alkyl, $C_2$–$C_6$-alkenyl, cyano, carboxy, $C_1$–$C_6$-alkyl, $C_1$–$C_6$-alkoxy, amino, $C_1$–$C_6$-alkylamino, di-$C_1$–$C_6$-alkylamino or hydrazino or
$R^1$ and $R^2$ together form a $C_2$–$C_6$-alkylidene or $C_3$–$C_6$-cycloalkylidene or
$R^1$ and $R^2$, together with the carbon atoms to which they are attached, form a $C_3$–$C_7$-spirocycle, n is 1,
$R^3$ is hydrogen, $C_1$–$C_8$-alkyl, $C_2$–$C_6$-alkenyl, $C_2$–$C_6$-alkynyl, $C_3$–$C_7$-cycloalkyl, benzyl, carboxy-$C_1$-$C_6$-alkyl, $C_1$-$C_6$-alkyloxycarbonyl-$C_1$-$C_6$-alkyl or di-$C_1$-$C_6$-alkyloxophosphinylmethyl, $R^4$, $R^5$, $R^6$ are the same or different and are hydrogen, a $C_1$-$C_7$-alkanesulphonyloxy, trifluoromethanesulphonyloxy, $C_1$-$C_7$-alkanesulphonyl-amino, trifluoromethanesulphonylamino, N-$C_1$-$C_7$-alkyl-$C_1$-$C_7$-alkanesulphonylamino, N-$C_1$-$C_7$-alkyl-trifluoromethanesulphonylamino, phenylsulphonylamino, $C_1$-$C_7$-alkylsulphenylmethyl, $C_1$-$C_7$-alkyl-sulphinylmethyl, $C_1$-$C_7$-alkylsulphenylmethyl, carboxy, $C_1$-$C_7$-alkoxy, $C_1$-$C_7$-alkyl, amino, $C_1$-$C_7$-alkylamino, di-$C_1$-$C_7$-alkylamino, sulphamyl, $C_1$-$C_7$-alkylamino, di-$C_1$-$C_7$-alkylamino, morpholino, thiomorpholino, pyrrolidino, piperidino, hexamethyleneimino, $C_1$-$C_7$-alkylcarbonylamino $C_1$-$C_7$-alkycarbonyloxy, aminocarbonylamino, $C_1$-$C_7$-alkylaminocarbonylamino, $C_1$-$C_7$-alkyl-mercapto, $C_1$-$C_7$-alkylsulphinyl, $C_1$-$C_7$-alkylsulphonyl, nitro, amino, hydroxyl, benzyloxy, $C_1$-$C_7$-alkoxy, $C_1$-$C_7$-alkyl, $C_2$-$C_7$-alkenyl, $C_2$-$C_7$-alkenyloxy, $C_2$-$C_7$-alkynyloxy, cyano-$C_1$-$C_7$-alkoxy, carboxy-$C_1$-$C_7$-alkoxy, phenyl-$C_1$-$C_7$-alkoxy, $C_1$-$C_7$-alkoxycarbonyl, $C_1$-$C_7$-alkoxy, $C_1$-$C_7$-alkylamino, di-$C_1$-$C_7$-alkylamino, trifluoromethyl, cyano, halogen or imidazolyl and when n=1 the benzimidazole ring is attached in the 5-, 7-, 8-position or, if $R^3$ is not hydrogen, further in the 6-position of the 1,2,3,4-tetrahydroquinolin-2-one, or their physiologically compatible salts and optical isomers.

2. Bicyclobenzimidazoles of claim 1, wherein $R^1$ is hydrogen or a $C_1$-$C_6$ alkyl group, $R_2$ is a $C_1$-$C_6$ alkyl group or $R^1$ and $R^2$, together with the carbon atom to which they are attached form a $C_3$-$C_7$ spirocycle.

3. Bicyclobenzimidazoles of formula I according to claim 1 or 2 wherein n is 1 and $R^3$ is hydrogen or $C_1$-$C_8$-alkyl, $C_2$-$C_6$-alkenyl, $C_2$-$C_6$-alkynyl, $C_3$-$C_7$-cycloalkyl, benzyl, carboxy-$C_1$-$C_6$-alkyl, $C_1$-$C_6$-alkoxycarbonyl-$C_1$-$C_6$-alkyl or di-$C_1$-$C_6$-alkyloxophosphinyl-$C_1$-$C_6$-alkyl, and wherein the benzimidazole ring is attached in the 5-, 7- or 8-position to the 1,2,3,4-tetrahydroquinoline-2-one.

4. Bicyclobenzimidazoles of formula I according to claim 1 or 2 wherein n 1 and $R^3$ is $C_1$-$C_8$-alkyl, $C_2$-$C_6$-alkenyl, $C_2$-$C_6$-alkynyl, $C_3$-$C_7$-cycloalkyl, benzyl, carboxy-$C_1$-$C_6$-alkyl, $C_1$-$C_6$-alkoxycarbonyl-$C_1$-$C_6$-alkyl or di-$C_1$-$C_6$-alkyloxophosphinyl-$C_1$-$C_6$-alkyl, wherein the benzimidazole ring is attached in the 5-, 6-, 7- or 8-position to the 1,2,3,4-tetrahydroquinoline-2-one.

5. Bicyclobenzimidazoles of formula I according to one of claims 1 or 2, wherein
$R^4$ is hydrogen, $C_1$-$C_4$ alkylsulphonyloxy, trifluoromethylsulphonyloxy, $C_1$-$C_4$ alkylsulphenylmethyl, $C_1$-$C_4$ alkylsulphinylmethyl, $C_1$-$C_4$ alkylsulphonylmethyl, $C_1$-$C_4$ alkylsulphonylamino, $C_1$-$C_4$ N-alkyl-alkylsulphonylamino, trifluoromethylsulphonylamino, $C_1$-$C_4$ N-alkyl-trifluoromethylsulphonylamino, carboxy, alkoxy, amino, $C_1$-$C_4$ alkylamino, $C_1$-$C_4$ dialkylamino sulfamyl, $C_1$-$C_4$ dialkylamino, morpholino, nitro, cyano, $C_1$-$C_4$ alkylaminosulphonyl, $C_1$-$C_4$ alkylcarbonylamino, $C_1$-$C_4$ alkylcarbonyloxy, aminocarbonylamino, $C_1$-$C_4$ N-alkylaminocarbonyl-amino, $C_1$-$C_4$ alkylmercapto, $C_1$-$C_4$ alkylsulphinyl, $C_1$-$C_4$ alkylsulphonyl, amino, hydroxy, benzyloxy, dialkylamino, $C_1$-$C_3$ alkyl, $C_1$-$C_3$ alkoxy, $C_1$-$C_3$ alkenyloxy, $C_1$-$C_3$ alkynyloxy, phenyl-$C_1$-$C_4$-alkoxy, cyanomethyloxy, methoxycarbonylmethyloxy, trifluoromethyl, 1-imidazolyl or halogen,
$R^5$ is hydrogen, hydroxyl, $C_1$-$C_3$ alkyl $C_1$-$C_4$ alkoxy, $C_1$-$C_4$ dialkylamino or halogen and
$R^6$ is alkoxy.

6. Bicyclobenzimidazoles according to one of claims 1 or 2 wherein $R^4$ is hydrogen, methanesulphonyloxy, trifluoromethanesulphonyloxy, methanesulphonylamino, trifluoromethanesulphonylamino, methanesulphonylmethylamino, trifluoromethanesulphonylmethylamino, methylsulphinylmethyl, methylsulphonylmethyl, aminocarbonyl, aminosulphonyl, methylaminosulphonyl, dimethylaminosulphonyl, acetylamino, methylmercapto, methylsulphinyl, methylsulphonyl, hydroxyl, allyloxy, methyl, methoxy, propargyloxy, cyanomethyloxy, methoxycarbonylmethyloxy, cyano, chloro, nitro, amino, dimethylamino, trifluoromethyl or 1-imidazolyl,
$R^5$ is hydrogen, methyl, methoxy, hydroxyl, dimethylamino or chlorine, $R^6$ is hydrogen or methyl and $R^2$ is methyl, ethyl or isopropyl or $R^1$ and $R^2$, together with the C-atoms to which they are attached, form a spirocyclopentyl ring, $R^3$ is hydrogen, methyl, ethyl, propyl, isopropyl, butyl, isobutenyl, allyl, ethoxycarbonyl or dimethyloxophosphinylmethyl.

7. Bicyclobenzimidazole of claim 1 wherein $R^4$ is
$C_1$-$C_2$-alkylsulphonyloxy,
$C_1$-$C_2$-alkylsulphenylmethyl,
$C_1$-$C_2$-alkylsulphinylmethyl,
$C_1$-$C_2$-alkylsulphonylmethyl,
$C_1$-$C_2$-alkylsulphonylamino,
$C_1$-$C_2$-N-alkyl-alkylsulphonylamino,
$C_1$-$C_2$-N-alkyl-trifluoromethylsulphonylamino,
a carbonyl substituted by
$C_1$-$C_2$ alkylamino or $C_1$-$C_2$ dialkylamino, a sulphonyl substituted by
$C_1$-$C_2$-dialkylamino, $C_1$-$C_2$-alkylmercapto, $C_1$-$C_2$-alkylsulphinyl, $C_1$-$C_2$ alkylsulphonyl and $R^5$ is $C_1$-$C_2$ alkoxy or $C_1$-$C_2$-dialkylamino.

8. Method for the treatment of disorders wherein a reduction of erythrocyte or thrombocyte aggregation is medically indicated comprising treating a patient with the disorder with a pharmaceutically acceptable amount of the compound of claim 1 or 2 in a pharmaceutically acceptable carrier.

9. Method for the treatment of disorders wherein a reduction of erythrocyte or thrombocyte aggregation is medically indicated comprising treating a patient in need of treatment with a pharmaceutically acceptable amount of a compound of claim 8 in a pharmaceutically acceptable carrier.

10. Method of claim 9 wherein the amount is 10–1500 mg/day/75 kg body weight.

11. A composition for the treatment of disorders wherein a reduction of erythrocyte or thrombocyte aggregation is medically indicated comprising a pharmaceutically acceptable amount of one or more of the compounds of claim 1 or 2 in a pharmacologically acceptable carrier.

12. A composition for the treatment of disorders wherein a reduction of erythrocyte or thrombocyte aggregation is medically indicated comprising a pharmaceutically acceptable amount of one or more of the compound of claim 8 in a pharmacologically acceptable carrier.

13. Bicyclobenzimidazoles of formula I according to any one of claims 1 or 2 selected from the group consisting of 2-(4,4-dimethyl-1,2,3,4-tetrahydro-2-oxo-7-quinolinyl)-benzimidazole and 2-(4,4-dimethyl-1-ethyl-1,2,3,4-tetrahydro-2-oxo-7-quinolinyl)-benzimidazole.

* * * * *

UNITED STATES PATENT AND TRADEMARK OFFICE
CERTIFICATE OF CORRECTION

PATENT NO. : 5,414,088
DATED : May 9, 1995
INVENTOR(S) : Von Der Saal et al.

It is certified that error appears in the above-indentified patent and that said Letters Patent is hereby corrected as shown below:

Column 8, line 52, after "trifluoroacetic" add --acid, methylene chloride or chloroform at temperatures--.

Signed and Sealed this

Twentieth Day of May, 1997

Attest:

BRUCE LEHMAN

Attesting Officer

Commissioner of Patents and Trademarks